US009101571B2

(12) United States Patent
Kuo et al.

(10) Patent No.: US 9,101,571 B2
(45) Date of Patent: Aug. 11, 2015

(54) PORCINE CIRCOVIRUS TYPE 2 (PCV2), IMMUNOGENIC COMPOSITION CONTAINING THE SAME, TEST KIT, AND APPLICATION THEREOF

(75) Inventors: Tsun-Yung Kuo, I-Lan (TW); Hsu Chung Gabriel Chen, Taipei (TW); Chung-Chin Wu, Wujie Township, I-Lan County (TW); Han-Ting Chen, Taoyuan (TW)

(73) Assignee: SBC VIRBAC LIMITED., Causeway Bay (HK)

( * ) Notice: Subject to any disclaimer, the term of this patent is extended or adjusted under 35 U.S.C. 154(b) by 138 days.

(21) Appl. No.: 13/332,269

(22) Filed: Dec. 20, 2011

(65) Prior Publication Data

US 2012/0164170 A1 Jun. 28, 2012

Related U.S. Application Data

(60) Provisional application No. 61/426,087, filed on Dec. 22, 2010.

(51) Int. Cl.

| | |
|---|---|
| ***A61K 39/12*** | (2006.01) |
| ***A01N 63/00*** | (2006.01) |
| ***C12Q 1/70*** | (2006.01) |
| ***C12N 15/01*** | (2006.01) |
| ***C12N 7/06*** | (2006.01) |
| ***G01N 33/569*** | (2006.01) |
| ***C07K 14/005*** | (2006.01) |
| ***C12N 7/00*** | (2006.01) |
| *A61K 39/00* | (2006.01) |

(52) U.S. Cl.

CPC ............... *A61K 39/12* (2013.01); *C07K 14/005* (2013.01); *C12N 7/00* (2013.01); *G01N 33/56983* (2013.01); *A61K 2039/5252* (2013.01); *A61K 2039/552* (2013.01); *A61K 2039/55566* (2013.01); *C12N 2750/00063* (2013.01); *C12N 2750/10021* (2013.01); *C12N 2750/10034* (2013.01); *G01N 2333/01* (2013.01)

(58) Field of Classification Search

None

See application file for complete search history.

(56) References Cited

U.S. PATENT DOCUMENTS

| | | | |
|---|---|---|---|
| 6,217,883 | B1 | 4/2001 | Allan et al. |
| 6,368,601 | B1 | 4/2002 | Allan et al. |
| 6,391,314 | B1 | 5/2002 | Allan et al. |
| 6,497,883 | B1 | 12/2002 | Bublot et al. |
| 6,517,843 | B1 | 2/2003 | Ellis et al. |

(Continued)

FOREIGN PATENT DOCUMENTS

TW 201014911 A1 4/2010

OTHER PUBLICATIONS

Guo et al., "Porcine circovirus type 2 (PCV2): genetic variation and newly emerging genotypes in China," Virology Journal, 7, pp. 273 (2010); also teaches Accession No. HM038017 cited in Result 8 of the STIC Search Result found in the SCORE file 20130213_144714_us-13-332-269.1.rge.*

(Continued)

*Primary Examiner* — Zachariah Lucas

*Assistant Examiner* — M. Franco Salvoza

(74) *Attorney, Agent, or Firm* — Locke Lord LLP; Tim Tingkang Xia, Esq.

(57) ABSTRACT

The invention relates to a novel porcine circovirus type 2 (PCV2) strain. The invention also relates to immunogenic compositions containing the novel PCV2 strain, PCV2 test kits, and applications of the novel PCV2 strain.

6 Claims, 6 Drawing Sheets

(56) References Cited

U.S. PATENT DOCUMENTS

| | | | | |
|---|---|---|---|---|
| 6,660,272 | B2 | 12/2003 | Allan et al. | |
| 6,943,152 | B1 | 9/2005 | Audonnet et al. | |
| 6,953,581 | B2 | 10/2005 | Allan et al. | |
| 7,122,192 | B2 | 10/2006 | Allan et al. | |
| 7,148,015 | B2 | 12/2006 | Jestin et al. | |
| 7,192,594 | B2 | 3/2007 | Haines et al. | |
| 7,211,379 | B2 | 5/2007 | Ellis et a | |
| 7,223,407 | B2 | 5/2007 | Jestin et al. | |
| 7,223,594 | B2 | 5/2007 | Jestin et al. | |
| 7,244,433 | B2 | 7/2007 | Jestin et al. | |
| 7,261,898 | B2 | 8/2007 | Jestin et al. | |
| 7,276,353 | B2 | 10/2007 | Meng et al. | |
| 7,279,166 | B2 | 10/2007 | Meng et al. | |
| 7,297,537 | B2 | 11/2007 | Jestin et al. | |
| 7,314,628 | B2 | 1/2008 | Jestin et al. | |
| 7,323,330 | B2 | 1/2008 | Jestin et al. | |
| 7,390,494 | B2 | 6/2008 | Jestin et al. | |
| 7,405,075 | B2 | 7/2008 | Jestin et al. | |
| 7,407,803 | B2 | 8/2008 | Jestin et al. | |
| 7,425,444 | B2 | 9/2008 | Jestin et al. | |
| 7,504,206 | B2 | 3/2009 | Haines et al. | |
| 7,575,752 | B2 | 8/2009 | Meng et al. | |
| 7,604,808 | B2 | 10/2009 | Jestin et al. | |
| 7,722,883 | B2 | 5/2010 | Jestin et al. | |
| 7,758,865 | B2 | 7/2010 | Jestin et al. | |
| 7,803,926 | B2 | 9/2010 | Haines et al. | |
| 7,829,273 | B2 | 11/2010 | Roof et al. | |
| 7,833,783 | B2 | 11/2010 | Haines et al. | |
| 2005/0147966 | A1* | 7/2005 | Meng et al. | 435/5 |
| 2010/0221283 | A1 | 9/2010 | Jestin et al. | |

OTHER PUBLICATIONS

Kixmoller et al., "Reduction of PMWS-associated clinical signs and co-infections by vaccination against PCV2," Vaccine 26: 3443-3451 (2008).*

Del Guidice et al., "Vaccine with the MF59 Adjuvant Do Not Stimulate Antibody Responses against Squalene," Clinical and Vaccine Immunology, vol. 13, No. 9: 1010-1013 (2006).*

Lytle et al., "Predicted Inactivation of Viruses of Relevance to Biodefense by Solar Radiation," J. Virol. 79(22): 14244-14252 (2005).*

Opreissnig et al., "Porcine Circovirus Type 2 Associated-Disease: Update on Current Terminology, Clinical Manifestations, Pathogenesis, Diagnosis, and Intervention Strategies," J Vet Diagn Invest 19:591-615 (2007).*

Duffy et al., "Rates of evolutionary change in viruses: patterns and determinants," Nature Reviews Genetics, vol. 9: 267-276 (2008).*

Rodriguez-Arrioja et al., Serum antibodies to porcine circovirus type 1 and type 2 in pigs with and without PMWS, The Veterinary Record, Jun. 24, 2000, 762-4,146, BMJ Group, UK.

Li,J., Shi,J.-L., Liu,Y. and Wang,J.-B., Porcine circovirus 2 isolate XT, complete genome, GenBank: HM161711, Sep. 4, 2010.

Xin,X., Huanchun,C. and Huaping,C., Porcine circovirus type 2 strain HB, complete genome, GenBank: AY291317.1, Jun. 2, 2003.

Zhai,S.L., Long,J.X., Wei,Z.Z., Zhang,J.W., Yue,C. and Yuan,S.S., Porcine circovirus 2 strain GX0839, complete genome, GenBank: GQ359002.1, Sep. 6, 2012.

Alderson T., The Mechanism of Formaldehyde-Induced Mutagenesis. The Monohydroxymethylation Reaction of Formaldehyde with Adenylic Acid as the Necessary and Sufficient Condition for the Mediation of the Mutagenic Activity of Formaldehyde, Mutat. Res. (1964) 106:77-85. Elsevier, U.S.A.

Broo K., J. Wei, D. Marshall, F. Brown, T. J. Smith, J. E. Johnson, A. Schneemann and G. Siuzdak, Viral capsid mobility: A dynamic conduit for inactivation, Proc. Natl. Acad. Sci. U.S.A. (2001) 98(5):2274-7. U.S.A.

Costa M., A. Zhitkovich, M. Harris, D. Paustenbach and M. Gargas, J., DNA-Protein Cross-Links Produced by Various Chemicals in Cultured Human Lymphoma Cells, Toxicology and Environmental Health (1997) 50(5): 433-449. Taylor & Francis, UK.

Feron V. J., H. P. Til, F. De Vrijer, R. A. Woutersen, F. R. Cassee and P. J. Van Bladeren, Aldehydes: occurrence, carcinogenic potential, mechanism of action and risk assessment, Mutat. Res. (1991) 259(3-4):363-85. Elsevier, U.S.A.

Fraenkel-Conrat H., Reaction of Nucleic Acid with Formaldehyde, Biochim. Biophys. Acta (1954) 15(2):307-9. ScienceDirect, U.S.A.

Gates K. S., T. Nooner and S. Dutta, Biologically Relevant Chemical Reactions of N7-Alkylguanine Residues in DNA, Chem. Res. Toxicol. (2004) 17(7):839-56. ACS Publications, U.S.A.

Grieb T., R. Y. Forng, R. Brown, T. Owolabi, E. Maddox, A. McBain, W. N. Drohan, D. M. Mann and W. H. Burgess, Effective use of Gamma Irradiation for Pathogen Inactivation of Monoclonal Antibody Preparations, Biologicals (2002) 30(3):207-216. Elsevier, U.S. A.

Kuykendall J. R. and M. S. Bogdanffy, Efficiency of DNA-histone crosslinking induced by saturated and unsaturated aldehydes in vitro, Mutat. Res. (1992) 283(2)131-6. Elsevier, U.S.A.

Lelie P. N., H. W. Reesink and C. J. Lucas, Inactivation of 12 viruses by heating steps applied during manufacture of a hepatitis B vaccine, J. Med. Virol. (1987) 23(3):297-301. Wiley, U.S.A.

Miller R. L. and P. G. Plagemann, Effect of Ultraviolet Light on Mengovirus: Formation of Uracil Dimers, Instability and Degradation of Capsid, and Covalent Linkage of Protein to Vial RNA, J. Virol. (1974) 13(3):729-39. American Society for Microbiology, U.S.A.

Permana P. A. and R. M. Snapka, Aldehyde-induced protein-DNA crosslinks disrupt specific stages of SV40 DNA replication, Carcinogenesis (1994) 15(5):1031-6. Oxford University Press, U.K.

Perrin P. and S. Morgeaux, Inactivation of DNA by Beta-propiolactone, Biologicals (1995) 23:207-211. The International Association of Biological Standardization, U.S.A.

Rutala W. A., D. J. Weber, and Hicpac, Guideline for Disinfection and Sterilization in Healthcare Facilities, 2008. CDC, USA, p. 43. U.S.A.

Schlegel A., A. Immelmann and C. Kempf, Virus inactivation of plasma-derived proteins by pasteurization in the presence of guanidine hydrockloride, Transfusion (2001) 41(3):382-9. Wiley, U.S.A.

Sinha R. P. and D. P. Hader, UV-induced DNA damage and repair: a review, Photochem. Photobiol. Sci. (2002) 1(4):225-36. Royal Society of Chemistry, U.K.

Subasinghe H. A. and P. C. Loh, Reovirus cytotoxicity: Some properties of the UV-irradiated reovirus and its capsid proteins, Arch. Gesamte. Virusforsch. (1972) 39(1):172-89. Wien ; New York, Springer-Verlag. U.S.A.

Weismiller D. G., L. S. Sturman, M. J. Buchmeier, J. O. Fleming and K. V. Holmes, Notes; Monoclonal Antibodies to the Peplomer Glycoprotein of Coronavirus Mouse Hepatitis Virus Identify Two Subunits and Detect a Conformational Change in the Subunit Released under Mild Alkaline Conditions, J. Virol. (1990) 64(6):3051-5. American Society for Microbiology, U.S.A.

* cited by examiner

```
H_strain_ORF2    MTYPRRRYRRRRHRPRSHLGQILRRRPWLVHPRHRYRWRRKNGIFNTRLSRTIGYTVKKT
ABV21950         MTYPRRRFRRRRHRPRSHLGQILRRRPWLVHPRHRYRWRRKNGIFNTRLSRTIGYTVKKT
ADK34046         MTYPRRRFRRRRHRPRSHLGQILRRRPWLVHPRHRYRWRRKNGIFNTRLSRTIGYTVKKT
ADD25772         MTYPRRRFRRRRHRPRSHLGQILRRRPWLVHPRHRYRWRRKNGIFNTRLSRTIGYTVKKT
                 *******:****************************************************

H_strain_ORF2    TVRTPSWNVDMMRFNINDFLPPGGGSSPLTVPFEYYRIRKVKVEFWPCSPITQGDRGVSS
ABV21950         TVRTPSWNVDMMRFNINDFLPPGGGSNPLTVPFEYYRIRKVKVEFWPCSPITQGDRGVGS
ADK34046         TVRTPSWNVDMMRFNINDFLPPGGGSNPLTVPFEYYRIRKVKVEFWPCSPITQGDRGVGS
ADD25772         TVRTPSWNVDMMRFNINDFLPPGGGSNPLTMPFEYYRIRKVKVEFWPCSPITQGDRGVGS
                 **************************.***:***************************.*

H_strain_ORF2    TAVILDDNFVTKANALTYDPYVNYSSRHTITQPFSYHSRYFTPKPVLDRTIDYFQPNNKR
ABV21950         TAVILDDNFVTKANALTYDPYVNYSSRHTITQPFSYHSRYFTPKPVLDRTIDYFQPN-KR
ADK34046         TAVILDDNFVTKANALTYDPYVNYSSRHTITQPFSYHSRYFTPKPVLDRTIDYFQPNNKR
ADD25772         TAVILDDNFVTKANALTYDPYVNYSSRHTITQPFSYHSRYFTPKPVLDRTIDYFQPNNKR
                 ********************************************************* **

H_strain_ORF2    NQLWLRLQTTGNVDHVGLGTAFENSIYDQDYNIRITMYVQFREFNLKDPPLNPK
ABV21950         NQLWLRLQTTGNVDHVGLGTAFENSIYDQDYNIRITMYVQFREFNLKDPPLNPK
ADK34046         NQLWLRLQTTGNIDHVGLGTAFENSIYDQDYNIRITMYVQFREFNLKDPPLNPK
ADD25772         NQLWLRLQTTGNVDHVGLGTAFENSIYDQDYNIRITMYVQFREFNLKDPPLNPK
                 ************:*****************************************
```

FIG.3

```
H_strain_ORF2      MTYPRRRYRRRRHRPRSHLGQILRRRPWLVHPRHRYRWRRKNGIFNTRLSRTIGYTVKKT
ADD25772_2d        MTYPRRRYRRRRHRPRSHLGQILRRRPWLVHPRHRYRWRRKNGIFNTRLSRTIGYTVKAT
                   ********************************************************** *

H_strain_ORF2      TVRTPSWNVDMMRFNINDFLPPGGGSSPLTVPFEYYRIRKVKVEFWPCSPITQGDRGVSS
ADD25772_2d        TVRTPSWAVDMMRFNINDFLPPGGGSNPLTVPFEYYRIRKVKVEFWPCSPITQGDRGVGS
                   ******* ******************.*******************************.*

H_strain_ORF2      TAVILDDNFVTKANALTYDPYVNYSSRHTITQPFSYHSRYFTPKPVLDRTIDYFQPNNKR
ADD25772_2d        TAVILDDNFVTKATALTYDPYVNYSSRHTIPQPFSYHSRYFTPKPVLDRTIDYFQPNNKR
                   *************.****************.*****************************

H_strain_ORF2      NQLWLRLQTTGNVDHVGLGTAFENSIYDQDYNIRITMYVQFREFNLKDPPLNPK
ADD25772_2d        NQLWLRLQTTGNVDHVGLGTAFENSIYDQDYNIRVTMYVQFREFNLKDPPLNPK
                   **********************************:*******************
```

PORCINE CIRCOVIRUS TYPE 2 (PCV2), IMMUNOGENIC COMPOSITION CONTAINING THE SAME, TEST KIT, AND APPLICATION THEREOF

The current application claims a priority to the U.S. 61/426,087 filed on Dec. 22, 2010.

BIOLOGICAL MATERIAL DEPOSIT

The isolated and purified porcine circovirus type 2 (PCV2) virus as disclosed and claimed has been deposited at China Center for Type Culture Collections, located at Wuhan University, Wuhan 430072, P.R. China, proofed by CCTCC Designation number "CCTCC V201117".

BACKGROUND OF THE INVENTION

1. Field of the Invention

The present invention relates to the field of animal healthcare, particularly to a novel porcine circovirus type 2 (PCV2) strain, an immunogenic composition containing the virus strain, PCV2 test kit, and application of the virus strain.

2. Description of the Prior Art

Porcine circovirus (PCV) was first discovered in a pig kidney cell line (PK-15, ATCC CCL33). Although the porcine circovirus can continuously contaminate PK-15 cells, the virus does not cause cytopathic effect (CPE) in the contaminated PK-15 cells. In addition, the PK-15-derived PCV is considered apathogenic. Even though the porcine circovirus can infect pigs, it does not cause lesions in the infected pigs. The porcine circovirus is an icosahedron-shaped, single-stranded DNA virus with a circular genome of 1,759 base pairs (bp). The PK-15-derived PCV was classified in the Circoviridae family in 1995.

In 1991, post-weaning multisystemic wasting syndrome (PMWS) was first recorded in pigs in Canada. PMWS affects 5- to 12-week-old piglets. It is clinically characterized by such symptoms as progressive weight loss, dyspnoea, pallor, and occasional jaundice. Its characteristic microscopic lesions include lymphoid depletion with histiocytic infiltrates within lymphoid organs, pneumonia, granulomatous inflammation, hepatitis, and nephritis. Since the 1991 outbreak in Canada, PMWS has been reported in many countries in North America, Europe, and Asia. Later, a new circovirus was isolated from pigs with PMWS. Whereas the morphology of the PMWS-derived porcine circovirus is very similar to that of the PK-15-derived PCV, the two porcine circoviruses share only 68 to 76% homology in their genome sequences. The apathogenic PK-15-derived PCV and the pathogenic PMWS-derived PCV were further identified as porcine circovirus type 1 (PCV1) and porcine circovirus type 2 (PCV2), respectively.

Porcine circovirus type 2 (PCV2) also belongs to the Circoviridae family. PCV2 is a nonenveloped, icosahedrons-shaped, single-stranded, circular DNA virus with a diameter of 17 nm, known to be one of the smallest animal viruses. The PCV2 circular genome contains the origin of replication with a stem loop structure, which is a common characteristic of circoviruses. The PCV2 genome comprises 1,767 or 1,768 nucleotides and is assumed to have 11 potential open reading frames (ORFs). Among the 11 ORFs, ORF 1 and ORF 2 are probably the most important genes, which encode replication (Rep and Rep') proteins and a capsid (Cap) protein, respectively. The capsid (Cap) protein encoded by PCV2 ORF2 gene would most likely be the antigen that induces production of neutralizing antibodies.

PCV2 infection is widespread on most of the pig farms in the world. PCV2 has been found to cause low survival rates and low feed conversion rates (FCRs) of infected pigs and result in great economic losses in pig farming Therefore, it is important to develop PCV2 test kits and vaccine against PCV2.

SUMMARY OF THE INVENTION

The first aspect of the present invention relates to a PCV2 strain, which was isolated from pigs showing clinical symptoms of post-weaning multisystemic wasting syndrome (PMWS), further analyzed and confirmed to be a novel PCV2 strain (PCV2 H strain). The positive (+) strand of the genome of the novel PCV2 strain (PCV2 H strain) has a DNA sequence of SEQ ID No. 1. The novel PCV2 strain has been deposited at the China Center for Type Culture Collection (CCTCC) on Nov. 5, 2011 under the accession number V201117.

The second aspect of the present invention relates to an immunogenic composition containing the novel PCV2 strain (PCV2 H strain). In one preferred embodiment, the immunogenic composition is a vaccine comprising an inactivated virus or an attenuated virus of the novel PCV2 strain (PCV2 H strain) and a pharmaceutically acceptable vehicle. However, the types of the vaccine include, but not limited to, inactivated vaccine, live (attenuated) vaccine (through virus attenuation), subunit vaccine, DNA vaccine, and other vaccines derived and produced from the novel PCV2 strain (PCV2 H strain) or from the DNA or amino acid sequences of the novel PCV2 strain (PCV2 H strain).

The inactivation process of the present invention includes, but not limited to, inactivation reagent treatment, heat treatment, and other treatments known to a person of ordinary skill in the art. The inactivation reagents include, but not limited to, formaldehyde, paraformaldehyde, beta-propiolactone (BPL), binary ethyleneimine (BEI), or other inactivation reagents suitable for the present invention.

The pharmaceutically acceptable vehicles include, but not limited to, solvent, emulsifier, suspending agent, decomposer, binding agent, excipient, stabilizing agent, chelating agent, diluent, gelling agent, preservative, lubricant, surfactant, adjuvant, or other suitable vehicles.

The adjuvant includes, but not limited to, oil adjuvant (such as mineral oil, plant oil, animal oil, Freund's Complete Adjuvant, Freund's Incomplete Adjuvant, etc.), aqueous adjuvant (such as aluminum hydroxide), biphasic emulsification adjuvant (such as water-in-oil-in-water emulsion adjuvant), biological adjuvant (such as CpG oligodeoxynucleotide and toxoid), etc. The biphasic emulsification adjuvant comprises a surfactant and an oleaginous substance. The surfactant is one or more than one selected from the group consisting of sorbitol fatty acid ester; the concentrate of sorbitol fatty acid ester and ethylene oxide (or propylene oxide); mannitol fatty acid ester; the concentrate of mannitol fatty acid ester and ethylene oxide (or propylene oxide); modified mannitol fatty acid ester with a hydrophilic group which is one or more than one selected from the group consisting of carboxylic acid, amine, amide, alcohol, polyol, ether, and oxide; anhydromannitol fatty acid ester; modified anhydromannitol fatty acid ester with a hydrophilic group which is one or more than one selected from the group consisting of carboxylic acid, amine, amide, alcohol, polyol, ether and oxide; saccharose fatty acid ester; the concentrate of saccharose fatty acid ester and ethylene oxide (or propylene oxide); glycerol fatty acid ester; the concentrate of glycerol fatty acid ester and ethylene oxide (or propylene oxide); the concentrate of fatty acid and ethylene oxide (or propylene oxide); the concentrate of fatty alcohol and ethylene oxide (or propylene oxide); and glycerophospholipid. The oleaginous substance is one or more than one selected from the group consisting of mineral oil, plant oil, and animal oil.

The immunogenic composition of the present invention further comprises at least one pathogen antigen. The pathogen antigens include, but not limited to, antigen of Swine influenza virus (SIV), antigen of porcine reproductive and respiratory syndrome virus (PRRSV), antigen of mycoplasma, antigen of porcine parvovirus (PPV), antigen of erysipelas, and antigen of pseudorabies (Aujeszky's disease) virus. The types of pathogen antigens include, but not limited to, recombinant proteins, subunit proteins, pathogens with gene defect, inactivated pathogen antigens, etc.

The third aspect of the present invention relates to a method of protecting pigs from PCV2 infection, including administering an immunologically effective dose of said PCV2 immunogenic composition to a pig to enhance its immunity against PCV2 infection, reduce severity of viremia and clinical symptoms, and increase survival rate and body weight.

The fourth aspect of the present invention relates to an anti-PCV2 antibody derived from the novel PCV2 strain (PCV2 H strain). The antibody includes, but not limited to, monoclonal antibodies, polyclonal antibodies, and genetically engineered antibodies. In one preferred embodiment, the antibody is a polyclonal antibody obtained via injecting an animal with the novel PCV2 strain (PCV2 H strain). In another preferred embodiment, the antibody is a monoclonal antibody obtained via screening a monoclonal hybridoma library.

The fifth aspect of the present invention relates to DNA fragments of the novel PCV2 strain (PCV2 H strain). The DNA fragments have nucleotide sequences of SEQ ID No. 1, 2, 4, and 6. Applications of the DNA fragments include, but not limited to, manufacturing of DNA vaccine and subunit vaccine, and designing primers or probes to detect PCV2 virus in a sample. In one preferred embodiment, the DNA fragment is the full-length genome sequence (SEQ ID No. 1) of the novel PCV2 strain (PCV2 H strain). In another preferred embodiment, the DNA fragments are the open reading frames (ORFs) of the novel PCV2 strain (PCV2 H strain), which include, but not limited to:

open reading frame 1 (ORF1) having a nucleotide sequence of SEQ ID No. 2, which encodes an amino acid sequence of SEQ ID No. 3, open reading frame 2 (ORF2) having a nucleotide sequence of SEQ ID No. 4, which encodes an amino acid sequence of SEQ ID No. 5, and open reading frame 3 (ORF3) having a nucleotide sequence of SEQ ID No. 6, which encodes an amino acid sequence of SEQ ID No. 7.

The sixth aspect of the present invention relates to a test kit for PCV2. The test kit is used to detect PCV2 virus or anti-PCV2 antibodies in a test sample. The test kit includes, but not limited to: (1) an antigen of the novel PCV2 strain (PCV2 H strain), in one preferred embodiment, the antigen is deposited on an antigen plate and inactivated with an inactivation reagent; (2) a monoclonal or polyclonal antibody derived from the novel PCV2 strain (PCV2 H strain); (3) a genetically engineered antigen or antibody derived from the full-length genome sequence (SEQ ID No. 1) or the nucleotide fragments (SEQ ID No. 2, 4, and 6) of the novel PCV2 strain (PCV2 H strain); and (4) a polynucleotide derived from the full-length genome sequence (SEQ ID No. 1) or the nucleotide fragments (SEQ ID No. 2, 4, and 6) of the novel PCV2 strain (PCV2 H strain). The polynucleotide includes, but not limited to, primers and probes. In one preferred embodiment, the polynucleotide is primers that can be used to detect the novel PCV2 strain (PCV2 H strain); and the primers have the nucleotide sequences of SEQ ID. No. 8 to 11.

The types of the test kit include, but not limited to, enzyme-linked immunosorbent assay kit (ELISA), microchip kit, immunofluorescent assay (IFA) kit, polymerase chain reaction (PCR) kit, and other test kits derived from the novel PCV2 strain (PCV2 H strain). In one preferred embodiment, the test kit comprises at least an antigen plate comprising the novel PCV2 strain (PCV2 H strain), and the test kit can be used to detect anti-PCV2 antibodies in a test sample.

The novel PCV2 strain (PCV2 H strain) of the present invention includes all the subcultured passages and the mutants that have the similar virus characteristics, genome, or pathogenicity as of the novel PCV2 strain (PCV2 H strain).

The terms "DNA", "nucleic acid", "nucleotide", and "polynucleotide" in the present invention relate to nucleic acid sequences in the natural, isolated, recombinant, or synthetic state.

The terms "amino acid", "peptide", "polypeptide", and "protein" in the present invention relate to amino acid sequences in the natural, isolated, recombinant, or synthetic state.

The terms "prevent", "protect", and "be against" relate to the observation that compared with the animals that are not vaccinated with the disclosed immunogenic composition, the animals vaccinated with the disclosed immunogenic composition can have an enhanced ability to against PCV2 infection, and the related diseases resulted from PCV2 infection.

The meaning of the technical and scientific terms as described herein can be clearly understood by a person of ordinary skill in the art.

The present invention is described in more detail in the following illustrative examples. Although the examples may represent only selected embodiments of the invention, it should be understood that the following examples are illustrative and not limiting.

BRIEF DESCRIPTION OF THE DRAWINGS

The present invention will be more easily understandable with the following detailed description and the accompanying drawings which are given by way of illustration only, and thus are not limitative of the present invention, and wherein:

FIG. 3: Alignment of ORF2 amino acid sequence (SEQ ID NO: 5) of PCV2 H strain and three other amino acid sequences (ABV21950, SEQ ID NO: 12; ADK34046, SEQ ID NO: 13; and ADD25772, SEQ ID NO: 14) that have the highest sequence similarities with ORF2 amino acid sequence (SEQ ID NO: 5) of PCV2 H strain in the GenBank database of National Center for Biotechnology Information (NCBI).

FIG. 4: Alignment of ORF2 amino acid sequence (SEQ ID NO: 5) of PCV2 H strain and ORF2 amino acid sequence (GenBank accession: ADD25772, SEQ ID NO: 14) of a prototype of PCV2 2d (GenBank accession: ZJ0955b).

DETAILED DESCRIPTION OF THE PREFERRED EMBODIMENT

Figure 1A:
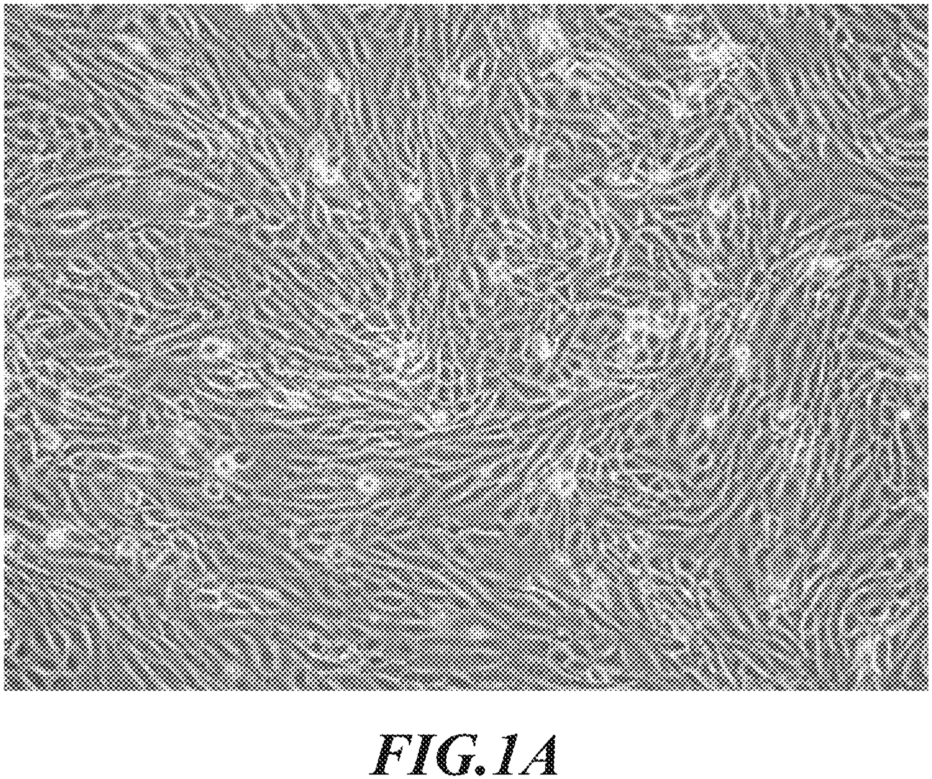
FIG. 1A: Uninfected PK-15 cells, cultured for 4 days (magnitude (100×))

The invention will be illustrated by way of the following examples, but the invention will not be limited thereto.

Example 1

Isolation and Identification of PCV2 Virus

1. Origin and Isolation of Seed Virus:

Tissue samples were collected from lung and lymph nodes of piglets in a pig farm in Hsin-Chu, Taiwan. These piglets were 8-week-old and showed clinical symptoms of post-weaning multisystemic wasting syndrome (PWMS). Lung and lymph node samples were collected and frozen at −70° C.

To isolate viruses, the tissue samples were homogenized, and 0.2 ml of each homogenate was inoculated into PK-15 monolayer cells or its derivative cell lines that are free of porcine circovirus (PCV), classical swine fever virus (CSFV), porcine adenovirus, porcine parvovirus, porcine reproductive and respiratory syndrome virus (PRRSV), pseudorabies virus (PRV), swine vesicular disease virus (SVDV), mycoplasma, and bacteria. After incubated for 1 hour at 37° C., 5% $CO_2$, the cells were washed three times with sterile phosphate buffered saline (PBS). Then, the cells were incubated with MEM medium containing 2% FBS for 4 hours at 37° C., 5% $CO_2$. After that, the MEM medium was discarded, and the cells were incubated with 300 mM D-glucosamine for 30 minutes. Then, the cells were washed three times with sterile PBS and incubated with MEM medium containing 8% FBS for 72 hours at 37° C., 5% $CO_2$. Finally, the cell cultures were tested for PCV2 with immunofluorescence assay (IFA).

IFA protocol is described as follows. First, sample cells were washed three times with sterile PBS, 5 minutes each time, and fixed with 75 μl of 80% acetone for 30 minutes at 4° C. Then, acetone was discarded, and the cells were washed three times with sterile PBS, 5 minutes each time. After that, the cells were incubated with 75 μl of porcine circovirus anti-viral polyclonal antiserum (VMRD®) (primary antibody, 1:1500 dilution in PBS) for 30 minutes at 37° C. Then, the antiserum was discarded, and the cells were washed three times with sterile PBS, 5 minutes each time. After that, the cells were incubated with 75 μl of rabbit anti-pig IgG-FITC (whole molecule) (Sigama, F1638) (secondary antibody, 1:1000 dilution in PBS) for 30 minutes at 37° C. Then, the antibody was discarded, and the cells were washed three times with sterile PBS, 5 minutes each time. Finally, each of the cell samples in a 96-well culture dish was mounted in 200 μl of PBS for fluorescent microscopic examination.

Virus that infected cells and yielded the most positive result of IFA was selected as seed virus. The genome sequence of the seed virus was then determined, as set forth in SEQ ID No. 1. The sequence was aligned, analyzed, and finally confirmed to be a new strain of PCV2 (analyses and results of sequence alignment are described below). This novel PCV2 strain is named PCV2 H strain.

2. Subculture of Seed Virus:

Freshly prepared PK-15 cells or its derivative cell lines were inoculated with the novel PCV2 strain (PCV2 H strain), and virus harvested from the inoculated cells was passage 1 ($P_1$) of PCV2 H strain. Supernatant of the cell culture, which contains $P_1$ of PCV2 H strain, was collected, diluted (1:2), and inoculated into freshly prepared PK-15 cells or its derivative cell lines. After the inoculated cells were incubated for 3 days, supernatant of the cell culture, which contains passage 2 ($P_2$) of PCV2 H strain, was collected, diluted (1:2), and inoculated into freshly prepared PK-15 cells or its derivative cell lines. The inoculated cells were incubated for 3 days; and supernatant of cell culture, which contains passage 3 ($P_3$) of PCV2 H strain, was next collected. The process was repeated three more times to obtain passage 6 ($P_6$) of PCV2 H strain.

Figure 1B:
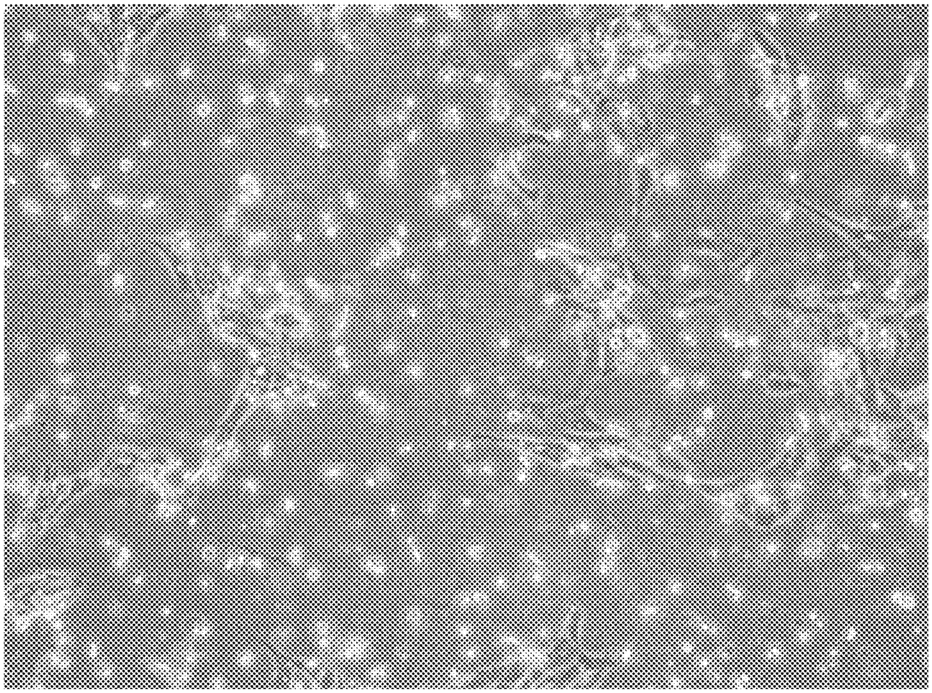
FIG. 1B: PK-15 cells infected with PCV2 H strain, cultured for 4 days (magnitude (100×)).

During the process of culturing PK-15 cells or its derivative cell lines that inoculated with PCV2 H strain, cytopathic effect (CPE) was observed in the inoculated cells, as shown in FIG. 1B. In addition, FIG. 1A shows the morphology and growth of non-inoculated PK-15 cells after 4 days of culturing (100×), whereas FIG. 1B shows the morphology and growth of PK-15 cells inoculated with PCV2 H strain after 4 days of culturing (100×). Similarly, the CPE observed in PK-15 derived cell lines that are inoculated with PCV2 H strain can be consulted in FIG. 1B for reference.

Figure 2:
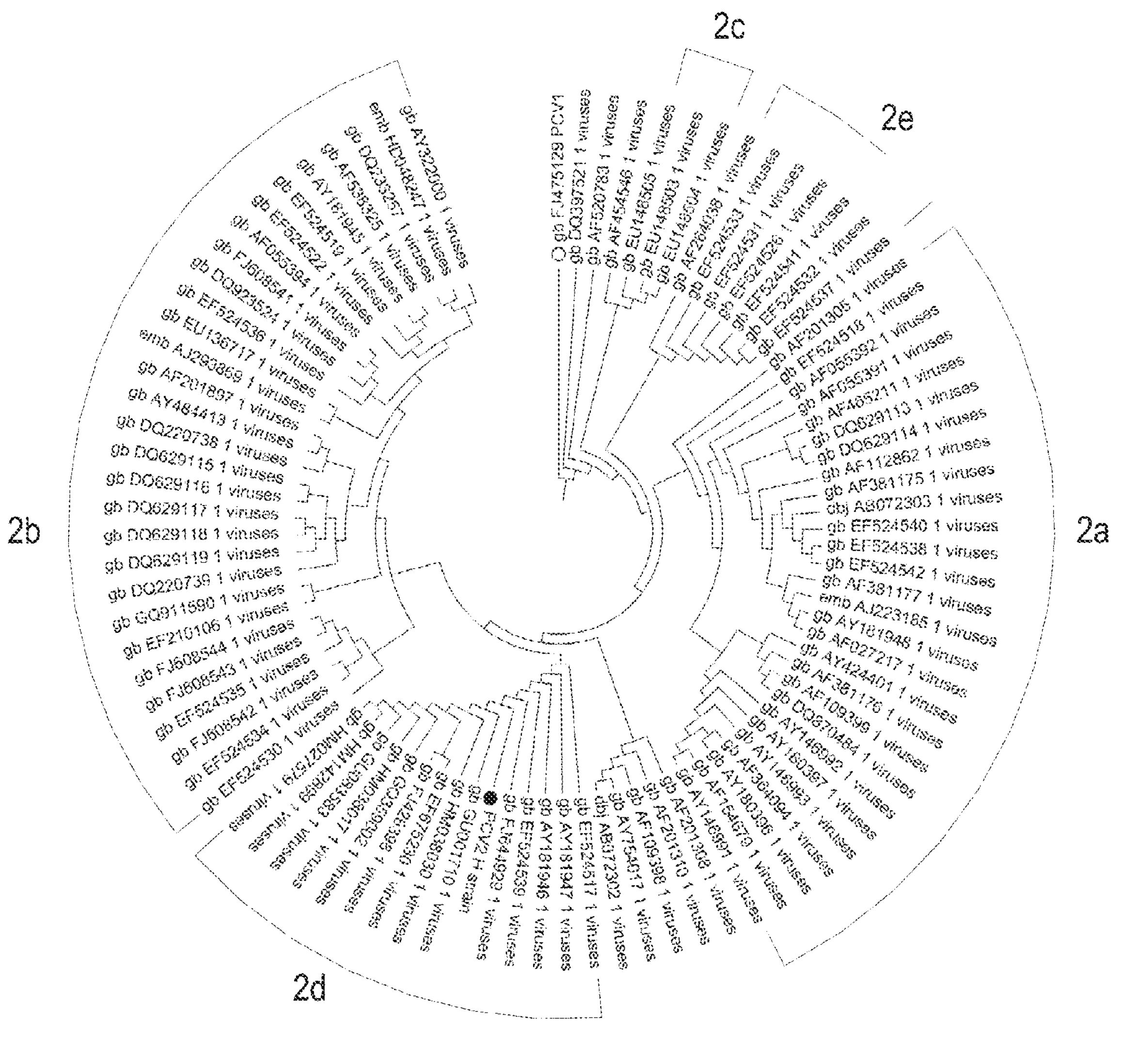
FIG. 2: Phylogenetic analysis of PCV2 H strain genome sequence.

3. Identification of Seed Virus:

The genome of PCV2 H strain isolated in the present invention has a nucleotide sequence of SEQ ID No. 1. The nucleotide sequence of SEQ ID No. 1 was compared with sequences in the GenBank database of the National Center for Biotechnology Information (NCBI). Results of the comparison show that PCV2 H strain was 99% homologous to some PCV2 sequences (Table 1), but there is no sequence in the database identical (100% homologous) to the genome sequence of PCV2 H strain (SEQ ID No. 1). Thus, based on the alignment results, the virus isolated in the present invention, PCV2 H strain, is shown to belong to PCV2 family and of a new strain. Based on the phylogenetic analysis of the genome sequence of PCV2 H strain shown in FIG. 2, PCV2 H strain is shown to be a member of PCV2 2d subgroup.

TABLE 1

Results of comparison of PCV2 H strain genomic DNA and sequences in the GenBank database of the NCBI by using the NCBI BLAST

| Accession No. | Description | Max score | Total score | Max ident. |
|---|---|---|---|---|
| HM038017.1 | Porcine circovirus 2 strain BDH | 3236 | 3236 | 99% |
| GU001710.1 | Porcine circovirus 2 isolate BJ0901b | 3236 | 3236 | 99% |
| EF675230.1 | Porcine circovirus 2 strain GXHZ-1 | 3236 | 3236 | 99% |
| GU083583.1 | Porcine circovirus 2 isolate PCV2C53 | 3230 | 3230 | 99% |
| GQ359002.1 | Porcine circovirus 2 strain GX0839 | 3230 | 3230 | 99% |
| FJ644929.1 | Porcine circovirus 2 isolate GL08 | 3230 | 3230 | 99% |
| FJ426398.1 | Porcine circovirus 2 strain GXWZ-1 | 3230 | 3230 | 99% |
| HM038030.1 | Porcine circovirus 2 strain AH | 3229 | 3229 | 99% |
| HM161710.1 | Porcine circovirus 2 isolate BX-2 | 3225 | 3225 | 99% |

An analysis shows that PCV2 H strain of the present invention has open reading frames (ORFs) 1, 2, and 3. The ORF1 has a nucleotide sequence of SEQ ID No. 2, which encodes amino acid sequence of SEQ ID No. 3. The ORF2 has a nucleotide sequence of SEQ ID No. 4, which encodes amino acid sequence of SEQ ID No. 5. The ORF3 has a nucleotide sequence of SEQ ID No. 6, which encodes amino acid sequence of SEQ ID No. 7.

Because the capsid protein encoded by PCV2 ORF2 gene would most likely be the antigen that induces production of neutralizing antibodies, the nucleotide sequence (SEQ ID NO: 4) and the amino acid sequence (SEQ ID NO: 5) of the ORF2 of PCV2 H strain were compared with sequences in the GenBank database of NCBI. The results of the comparison show that no sequence in the GenBank database of NCBI is identical (100% homologous) to the nucleotide sequence (SEQ ID NO: 4) or the amino acid sequence (SEQ ID NO: 5) of ORF2 of PCV2 H strain. The highest homology between the amino acid sequence of the ORF2 of PCV2 H strain (SEQ ID NO: 5) and sequences in the Genbank database is 98%. FIG. 3 shows the alignment of the amino acid sequence of ORF2 of PCV2 H strain (SEQ ID NO: 5) and the top three sequences of the highest homology (SEQ ID NOs: 12, 13, and 14), and the alignment indicates that there are 6 amino acids of SEQ ID NO: 5 different from the top three sequences. The amino acid sequence (SEQ ID NO: 5) of ORF2 of PCV2 H strain was further compared with the amino acid sequence (GenBank Accession: ADD25772, SEQ ID NO: 14) of ORF2 of a PCV2 2d subgroup prototype (GenBank Accession: ZJ0955b), and the result, shown in FIG. 4, indicates that there are 7 amino acids different between the two sequences, and the two sequences share 97% homology.

In addition, the nucleotide sequences (SEQ ID No. 2 and 6) and the amino acid sequences (SEQ ID No. 3 and 7) of the ORF1 and ORF3 of PCV2 H strain were compared with sequences in the GenBank database of NCBI. The results of the comparison show that no sequence in the GenBank database of NCBI is identical (100% homologous) to the nucleotide sequences or the amino acid sequences of ORF1 or ORF3 of PCV2 H strain.

The analyses indicate that PCV2 H strain of the present invention is a novel strain of porcine circovirus type 2 (PCV2). The novel PCV2 strain has been deposited at the China Center for Type Culture Collection (CCTCC) on Nov. 5, 2011 under the accession number V201117.

Example 2

Preparation of PCV2 H Strain Vaccine

1. Virus Cultivation

PK-15 cells free of porcine circovirus (PCV), classical swine fever virus (CSFV), porcine adenovirus, porcine parvovirus, porcine reproductive and respiratory syndrome virus (PRRSV), pseudorabies virus (PRV), swine vesicular disease virus (SVDV), mycoplasma, and bacteria were cultured in cell culture growth medium (MEM medium containing 5% FBS, pH 7.2±0.2) at 37° C., 5% $CO_2$. After a monolayer of PK-15 cells was formed, the PK-15 cells were dissociated with 0.2% trypsin-EDTA and suspended in cell culture maintenance medium (MEM medium containing 2% FBS, pH 7.4±0.2) for cell counting. Then, the cells were diluted with cell culture growth medium to a final concentration of $3.0\times10^5$ cells/ml, and allocated to roller bottles for culturing for 3~4 days at 37° C. to reach a confluent monolayer. After that, cell culture medium inside the roller bottles was discarded and the cells were washed with PBS. Viral stock of PCV2 H strain was diluted with cell culture maintenance medium to a final concentration of $10^{4.0}$ $TCID_{50}$/ml and inoculated onto the monolayers of PK-15 cells in the roller bottles. For virus cultivation, the infected cells was incubated for 48~96 hours at 37° C. Virus titer of PCV2 H strain was monitored by immunofluorescence assay (IFA). Then, in order to collect virus solution of PCV2 H strain, the supernatant of the cell cultures was harvested when the virus titer reached $10^{6.0}$ $TCID_{50}$/ml or higher, or when cytopathic effect (CPE) reached 70-80%.

2. Antigen Inactivation

Thirty-seven percent (37%, by weight) formaldehyde was added to the virus solution of PCV2 H strain collected in the above-mentioned step to a final concentration of 0.2% (w/v), and then the virus was inactivated by continuously shaking with formaldehyde for at least 24 hours, preferably 48 hours, at 37° C. After the virus was completely inactivated, the virus solution of PCV2 H strain containing formaldehyde was centrifuged to remove formaldehyde. Then, the centrifuged virus solution was suspended in buffer solution, such as distilled water or phosphate buffered saline (PBS), and the suspended virus solution was the inactivated antigen stock of PCV2 H strain inactivated vaccine and stored at 4° C. for later use.

3. Preparation of PCV2 H Strain Inactivated Vaccine

A sterilized biphasic emulsification adjuvant, such as MONTANIDE™ ISA 206 oily vaccine adjuvant for water-in-oil-in-water (W/O/W) emulsion, was added to the inactivated antigen stock of PCV2 H strain inactivated vaccine to a final concentration of 50% (v/v) in an emulsion tank for mixing and emulsification. The emulsified product is PCV2 H strain inactivated vaccine with oil-adjuvant.

Other suitable adjuvants for the PCV2 inactivated vaccine of the present invention known to those skilled in the art can also be used as the adjuvant in the present invention. The biphasic emulsification adjuvant (such as water-in-oil-in-water emulsion adjuvant) used in this example can be replaced with, but not limited to, oil adjuvant (such as mineral oil, plant oil, animal oil, Freund's Complete Adjuvant, Freund's Incomplete Adjuvant, etc.), aqueous adjuvant (such as aluminum hydroxide), or biological adjuvant (such as CpG oligodeoxynucleotide and toxoid).

Example 3

Preparation of PCV2 Test Kit-1

The PCV2 test kit in this example is an antigen plate containing the viral antigen of PCV2 H strain. First, PK-15 cells or its monoclonal cell lines were cultured, trypsinized, and resuspended in cell culture medium at a final concentration of $2\times10^5$ cells/ml. Fifty microliter (μl) of the PK-15 cells and 50 nl viral stock of PCV2 H strain ($1\times10^3$ $TCID_{50}$/ml) were added to each well of a 96-well cell culture plate (flat bottom) and incubated for 72 hours at 37° C., 5% $CO_2$. The cells infected with PCV2 H strain were washed twice with sterilized PBS and fixed with 80% acetone for 15 minutes at room temperature. Then acetone was discarded, and the cells were washed three times with sterilized PBS. After that, the plate was inverted and next dried in a 37° C. incubator. The dried plate is the antigen plate containing the viral antigen of PCV2 H strain, and it can be used for ELISA test to detect the amount of antibodies against PCV2 in a serum sample. The plate then was stored at −20° C. for later use.

Example 4

Preparation of PCV2 Test Kit-2

The PCV2 test kit in this example is an antigen plate containing a recombinant capsid protein of PCV2 H strain. The recombinant capsid protein is the antigen of the antigen plate. The capsid protein is encoded by the ORF2 gene of PCV2 H strain and has the amino acid sequence of SEQ ID No. 5.

The ORF2 nucleotide sequence of PCV2 H strain was first amplified by polymerase chain reaction (PCR). Viral DNA of the PCV2 H strain was used as the template DNA in the PCR reaction. A forward primer and a reverse primer were designed to amplify the ORF2 nucleotide sequence. The forward primer in this example has a HindIII cleavage site, and the reverse primer in this example has an Xho I cleavage site.

The primers can be designed according to the ORF2 nucleotide sequence (SEQ ID No. 4) of the present invention by those skilled in the art. For the PCR reaction, a PCR mixture containing 8 μl of template DNA, 5 μl of 10× PCR buffer (MDBio, Inc.), 8 μl of dNTPs (each at 1.25 mM), 1 μl of each primer (each at 50 μM), and 0.5 μl of Pfu DNA polymerase (MDBio, Inc.) in a final volume of 50 μl was placed in a GeneAmp PCR System 2400 reactor (Applied Biosystems). The PCR reaction started with an initial step of pre-heating the PCR mixture at 95° C. for 5 minutes, and amplification of DNA was carried out by 25 cycles with the following parameters; denaturing at 95° C. for 30 seconds, annealing at 55° C. for 30 seconds, and elongating at 72° C. for 30 seconds. The PCR reaction was completed with a final extension step of 5 minutes at 72° C. PCR products were purified with PCR-M Clean Up Kit (Viogene).

After purification, the PCR products were constructed into a pET24a expression vector. The purified PCR products and pET24a expression vector (Novagen) were digested with two restriction enzymes (New England Biolabs), Hind III and Xho I, respectively for 8 hours at 37° C. After restriction enzyme cleavage reaction, the digested PCR products and pET24a expression vector were purified with PCR-M Clean Up Kit (Viogene) respectively. The purified PCR products were ligated with the purified pET24a expression vector, and the ligation product was transformed into host cells (*E. coli*). Transformants were selected, and a clone with the correct sequence was identified by DNA sequencing and named pET24a-ORF2.

The bacteria with pET24a-ORF2 were cultured in 2 ml of LB broth for 16 to 18 hours at 37° C., and then the culture was added to fresh LB broth containing 25 μg/ml kanamycin at a ratio of 1:50 and cultured at 37° C., 200 rpm. When the optical density at a wavelength of 600 nm (OD600) of the culture reached 0.6, isopropyl-β-D-thiogalactoside (IPTG) was added to the culture to a final concentration of 1 mM, and the culture was incubated for 6 more hours at 37° C., 200 rpm. One milliliter of the culture was centrifuged (10,000×g) and next determined whether the recombinant proteins were soluble proteins or inclusion body with B-PER™ Bacterial Protein Extraction (Pierce Protein Research Produces). Forty microliters (μl) of reagent were added to the centrifuged bacteria and shaken on a vortex mixer for 1 minute. The mixture was then centrifuged at 10,000×g. The proteins suspend in the supernatant were soluble proteins, whereas the proteins in the lower part (pellets) were inclusion bodies. The soluble proteins were dissolved in 1× sample buffer for SDS-PAGE analysis, whereas the inclusion bodies were mixed with 2× sample buffer for SDS-PAGE analysis. Both samples were boiled for 20 minutes and then centrifuged. Proteins in the supernatant of both samples were resolved with 15% SDS-PAGE to analyze the expression of the recombinant capsid protein of PCV2 H strain. After the analyses, the recombinant capsid protein of PCV2 H strain was used to make antigen plates.

The recombinant capsid protein of PCV2 H strain was diluted with PBS (pH 9.6) to a final concentration of 10 μg/ml. The diluted recombinant protein was coated on a 96-well cell culture plate (flat bottom) (100 μL/well) at 37° C. for 2 hours and then at 4° C. overnight. After that, each well of the plate was washed three times with PBS for 3 to 5 minutes and added 200 μl of 0.15% BSA blocking solution to block the recombinant protein for 2 hours at 37° C. After each well of the plate was washed with PBS, the plate was stored at 4° C. for later use.

Example 5

Preparation of Anti-PCV2 H Strain Antibodies

1. Anti-PCV2 H Strain Polyclonal Antibodies

Inactivated PCV2 H strain with sufficient virus titer was mixed with a suitable adjuvant, such as Freund's Complete Adjuvant. The mixture was primarily inoculated into animals, such as mice, pigs, goats, and rabbits, and a second immunization may be performed after an appropriate time period (such as 2 to 3 weeks) if necessary. After another appropriate time period (such as 2 to 3 weeks), serum of the inoculated animals was collected as anti-PCV2 H strain polyclonal antibodies.

The anti-PCV2 H strain polyclonal antibodies can be conjugated to chromogenic reporters or fluorescence if necessary.

The inoculated animals can be further vaccinated to boost antibody titer after primary or second immunization if necessary.

Animals that can be inoculated to produce anti-PCV2 H strain polyclonal antibodies include, but not limited to, mice, rabbits, avian (eggs), pigs, goats, cattle, and aqua animals.

2. Anti-PCV2 H Strain Monoclonal Antibodies

Inactivated PCV2 H strain with a sufficient virus titer or a specific antigen fragment (such as ORF2) of PCV2 H strain was primarily inoculated into an animal (such as a mouse). The inactivated virus or antigen fragment can be mixed with a suitable adjuvant, such as Freund's Complete Adjuvant, if necessary. Also, a second immunization may be performed after an appropriate time period (such as 2 to 3 weeks) if necessary. After another appropriate time period (such as 2 to 3 weeks), serum of the inoculated animal was collected to evaluate whether the animal's spleen cells were suitable for producing anti-PCV2 H strain monoclonal antibodies. Cell fusion of the suitable spleen cells collected from the inoculated animal and myeloma cells (such as FO cell line and NS cell line) was accomplished using polyethylene glycol (PEG, such as PEG1500). Hybridomas that produce antibodies of appropriate specificity were selected from fused cells and next subcloned to be hybridomas that are suitable to produce anti-PCV2 H strain monoclonal antibodies.

The anti-PCV2 H strain monoclonal antibodies can be used in test kits, therapy, or food or feed supplement to enhance animals' immunity.

Example 6

Efficacy Trial of Inactivated PCV2 Vaccine-1

1. Vaccination Protocol and Sample Collection

Five- to six-week-old specific-pathogen-free (SPF) Balb/c mice were randomly divided into 4 groups of 15 mice each. ELISA test showed that all the 60 mice were negative for anti-PCV2 antibodies. The mice in the 3 vaccine groups (Groups 1 to 3) were injected intramuscularly with 0.2 ml of 3 different lots of inactivated PCV2 H strain vaccine, respectively. Two weeks after primary immunization (p.i.), the mice in the 3 vaccine groups were boosted with the same dose of the 3 different lots of vaccine. Mice in Group 4 were unvaccinated and served as negative control. At 2, 3, 4, and 5 weeks after the primary immunization (p.i.), 5 mice from each group were randomly selected to collect serum samples. All the serum samples were tested by ELISA.

2. Detection of anti-PCV2 Antibodies by ELISA

The antigen plates prepared in Example 3 or 4 can be used as the ELISA plates in this example. The ELISA plates were washed 3 times with 50 mmol/L PBS (pH 7.2) containing 500 μl/L Tween-20 (i.e. PBST) for 3 to 5 minutes each time. To block the ELISA plates, 200 μL of 0.15% BSA blocking solution was added to each well of the ELISA plates, and then the ELISA plates were incubated for 2 hours at 37° C. After that, the ELISA plates were washed with PBS. Mice serum samples were diluted fifty-fold (1:50) with PBS and then diluted two-fold serially. Diluted serum samples were added to the wells of the ELISA plates (100 μl/well), and the plates were incubated for 1 hour at 37° C. After incubation, the plates were washed with PBS. Secondary antibody (such as rabbit anti-mouse secondary antibody) conjugated to horseradish peroxidase (HRP) was then added to the wells. After incubating for 1 hour at 37° C., the plates were washed with PBS. For visualization of results, 3,3',5,5'-tetramethylbenzidine (TMB) was added to the wells. Following incubation, the reaction was stopped by adding 2 mM $H_2SO_4$. Results were reported as positive-to-negative (P/N) ratios. The P/N ratio was calculated by dividing optical density at 450 nm ($OD_{450}$) of a given test sample by the $OD_{450}$ of the standard negative control. P/N ratios ≥2.1 were considered positive. The maximum dilutions of P/N ratios ≥2.1 were considered the ELISA antibody titers of the serum samples.

In addition to HRP and TMB, other chromogenic reporters or fluorescence with the same function, such as alkaline phosphatase (AP), 4-methylumbelliferyl phosphate (4-MUP), and fluorescein isothiocyanate (FITC), can also be used in this example.

3. Results

Figure 5:
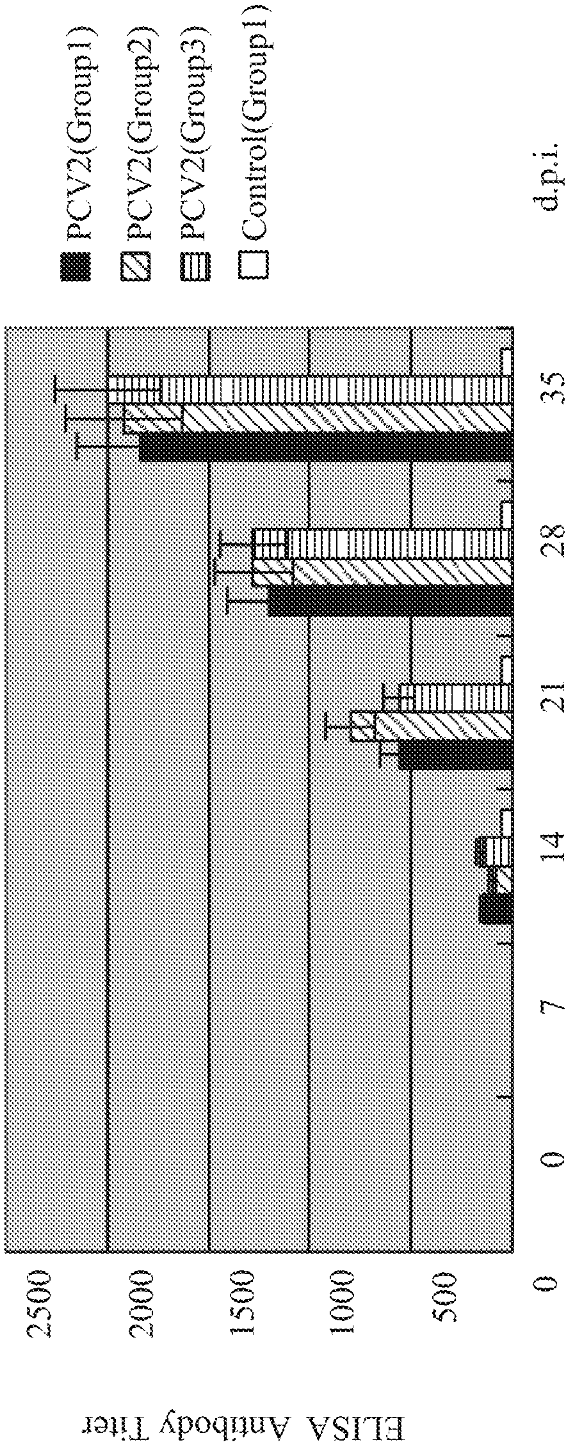
FIG. 5: Results of PCV2 ELISA of serum samples collected at different time points from mice vaccinated with PCV2 H strain inactivated vaccine.

At 2 weeks after the primary immunization (p.i.), anti-PCV2 H strain antibodies were detected in all vaccinated mice. After second immunization, the ELISA antibody titers of vaccinated mice reached 1800 to 2000 at 35 day after the primary immunization (d.p.i.) (FIG. 5). Therefore, the results indicated that the inactivated PCV2 H strain vaccine of the present invention was able to effectively induce immune responses in mice.

Example 7

Efficacy Trial of Inactivated PCV2 Vaccine-2

1. Vaccination Protocol and Sample Collection

Two healthy piglets that were 5- to 6-week-old were injected intramuscularly with 1 ml of inactivated PCV2 H strain vaccine, respectively. Three weeks after the primary immunization (p.i.), the piglets were boosted with the same dose of the vaccine. Serum samples were collected from both piglets before the primary immunization (5- to 6-week-old), before the second immunization (8- to 9-week-old), and at 2 weeks after the second immunization (10- to 11-week-old). Both piglets were weighed at the same time points as serum collection. All the serum samples were tested by ELISA.

2. Detection of Anti-PCV2 Antibodies by ELISA

The antigen plates prepared in Example 3 or 4 can be used as the ELISA plates in this example. The ELISA plates were washed 3 times with 50 mmol/L PBS (pH 7.2) containing 500 μl/L Tween-20 (i.e. PBST) for 3 to 5 minutes each time. To block the ELISA plates, 200 μL of 0.15% BSA blocking solution was added to each well of the ELISA plates, and then the ELISA plates were incubated for 2 hours at 37° C. After that, the ELISA plates were washed with PBS. Pig serum samples were diluted fifty-fold (1:50) with PBS and then diluted two-fold serially. Diluted serum samples were added to the wells of the ELISA plates (100 μl/well), and the plates were incubated for 1 hour at 37° C. After incubation, the plates were washed with PBS. Secondary antibody (such as goat anti-pig secondary antibody) conjugated to horseradish peroxidase (HRP) was then added to the wells. After incubating for 1 hour at 37° C., the plates were washed with PBS. For visualization of results, 3,3',5,5'-tetramethylbenzidine (TMB) was added to the wells. Following incubation, the reaction was stopped by adding 2 mM $H_2SO_4$. Results were reported as positive-to-negative (P/N) ratios. The P/N ratio was calculated by dividing optical density at 450 nm ($OD_{450}$) of a given test sample by the $OD_{450}$ of the standard negative control. P/N ratios ≥2.1 were considered positive. The maximum dilutions of P/N ratios ≥2.1 were considered the ELISA antibody titers of the serum samples.

3. Results

At 3 weeks after the primary immunization (p.i.), anti-PCV2 H strain antibodies were detected in both vaccinated piglets. At 2 weeks after the second immunization, the ELISA antibody titers of vaccinated piglets were higher than 11,000 (Table 2). Therefore, the results indicated that the inactivated PCV2 H strain vaccine of the present invention was able to effectively induce immune responses in pigs.

TABLE 2

ELISA antibody titers of vaccinated piglets

| Sampling Time Points | Before the primary immunization (5- to 6-week-old) | Before the second immunization (8- to 9-week-old) | At 2 weeks after the second immunization (10- to 11-week-old) |
|---|---|---|---|
| Piglet 1 | 1 | 8,490 | 11,728 |
| Piglet 2 | 1 | 10,263 | 13,065 |

Example 8

Efficacy Trial of Inactivated PCV2 Vaccine-3

1. Vaccination Protocol and Sample Collection

Forty healthy piglets that were 2-week-old were randomly divided into 4 groups of 10 piglets each. At the age of 3 weeks, piglets in the 3 vaccine groups (Groups 1 to 3) were injected intramuscularly with 1 ml of 3 different lots of inactivated PCV2 H strain vaccine, respectively. Three weeks after the primary immunization (p.i.), the piglets were boosted with the same dose of the vaccine. Piglets in Group 4 were unvaccinated and served as negative control. Serum samples were collected from all the piglets at 1 week before the primary immunization (2-week-old) and at 1, 2, 3, and 5 weeks after the primary immunization (4-, 5-, 6-, and 8-week-old respectively). All of the piglets were weighed at the ages of 3, 4, 5, 6, and 8 weeks. All the serum samples were tested by ELISA.

TABLE 3

Schedule of vaccination and sample collection

| Ages (weeks) | 2 | 3 | 4 | 5 | 6 | 8 |
|---|---|---|---|---|---|---|
| Vaccination | — | Primary Vaccination | — | — | Second vaccination | — |

TABLE 3-continued

| Schedule of vaccination and sample collection | | | | | | |
|---|---|---|---|---|---|---|
| Ages (weeks) | 2 | 3 | 4 | 5 | 6 | 8 |
| Test 1 | Blood sampling, IFA | — | Blood sampling, IFA | Blood sampling, IFA | Blood sampling, IFA | Blood sampling, IFA |
| Test 2 | — | Weighing | Weighing | Weighing | Weighing | Weighing |

2. Detection of Anti-PCV2 Antibodies by IFA

The antigen plates prepared in Example 3 were used in this example. The antigen plates were taken from −20° C. to thaw and dry at 37° C. Pig serum samples were diluted fifty-fold (1:50) with PBS and then diluted two-fold serially. Diluted serum samples were added to the wells of the antigen plates (50 μl/well), and the plates were incubated for 30 minutes at 37° C. After incubation, the plates were washed 3 times with PBS to remove uncombined antibodies. Fifty microliters (50 μl) of rabbit anti-pig IgG conjugated to FITC (1:100, Sigma) was then added to the wells. After incubated in the dark for 30 minutes, the plates were washed 3 times with PBS and examined under a fluorescence microscope to calculate titer of anti-PCV2 H strain antibodies. (Rodriguez-Arrioja et al., 2000)

3. Results 3.1 Antibody Titer

Figure 6:
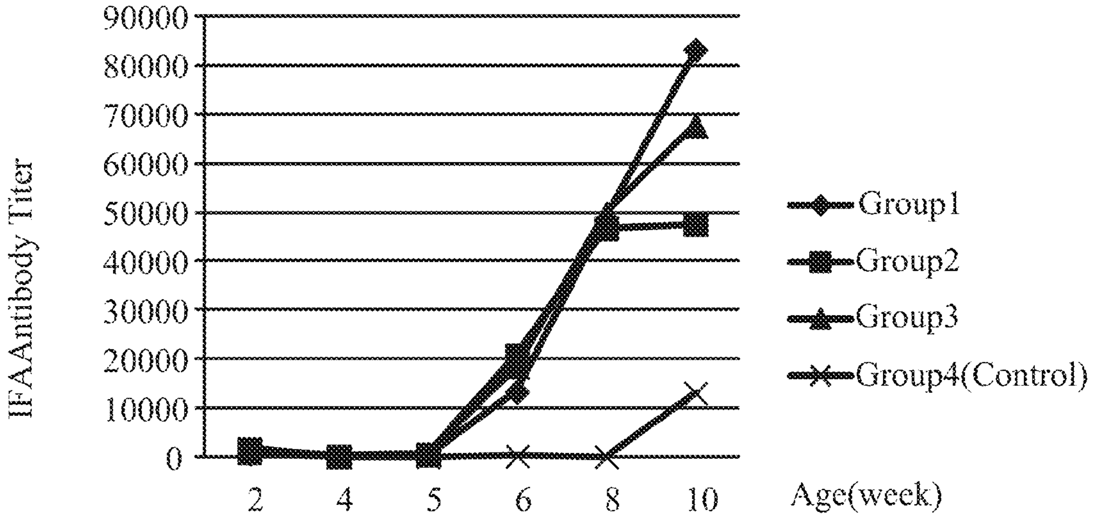
FIG. 6: Results of PCV2 IFA of serum samples collected at different time points from piglets vaccinated with PCV2 H strain inactivated vaccine.

At 2 weeks after the primary immunization (p.i.), serum samples from vaccinated piglets (at the age of 5 weeks) had IFA titers around 600, while serum samples from control group had IFA titers about 200 (Table 4 and FIG. 6). After the second immunization, IFA titers in vaccinated piglets (at the age of 6 weeks) increased dramatically (IFA titers are higher than 13,000). At the age of 8 weeks, vaccinated piglets had IFA titers higher than 46,000, while the unvaccinated piglets had very low IFA titers around 170.

TABLE 4

| Anti-PCV2 H strain antibody titers of vaccinated piglets by IFA | | | | | |
|---|---|---|---|---|---|
| Age (week) | 2 | 4 | 5 | 6 | 8 |
| Group 1 | 800 | 200 | 600 | 13,440 | 48,640 |
| Group 2 | 1,680 | 230 | 620 | 20,800 | 46,720 |
| Group 3 | 1,100 | 220 | 650 | 18,660 | 49,760 |
| Group 4 (Control) | 1,880 | 210 | 190 | 300 | 170 |

3.2 Weight Gain

Figure 7:
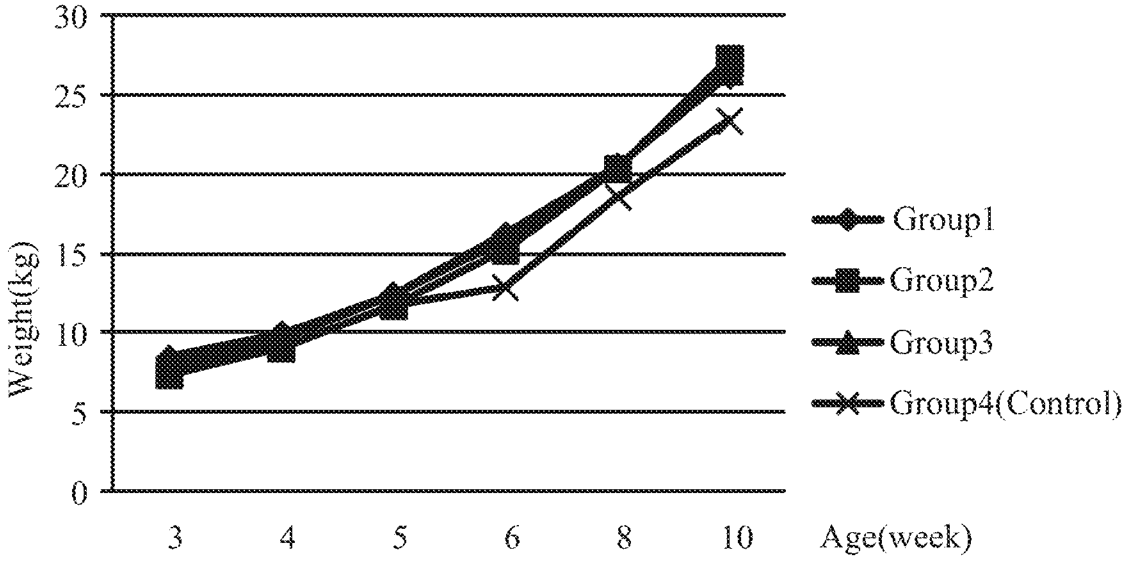
FIG. 7: Body weights of piglets vaccinated with PCV2 H strain inactivated vaccine.

Vaccinated piglets had higher weight gains than did the unvaccinated piglets in the control group (Table 5 and FIG. 7). At the age of 8 weeks, vaccinated piglets were around 2 kg heavier than the unvaccinated piglets.

TABLE 5

| Body weights of vaccinated piglets (kg) | | | | | |
|---|---|---|---|---|---|
| Age (week) | 3 | 4 | 5 | 6 | 8 |
| Group 1 | 8.4461 | 9.9512 | 12.4207 | 16.1756 | 20.5284 |
| Group 2 | 7.3781 | 9.064 | 11.7594 | 15.2267 | 20.3755 |
| Group 3 | 7.9564 | 9.5413 | 12.3461 | 15.8561 | 20.4345 |
| Group 4 (Control) | 7.5906 | 8.9899 | 11.724 | 12.9102 | 18.6059 |

Therefore, the results indicated that the inactivated PCV2 H strain vaccine of the present invention was able to effectively induce immune responses in pigs, enhance immunity in pigs, and then increase weight gain in pigs.

Example 9

Efficacy Trial of Inactivated PCV2 Vaccine-4

1. Vaccination Protocol and PCV2 Infection

Fourteen- to sixteen-day-old piglets were randomly divided into 4 groups of 5 piglets each. All the 20 piglets were negative for anti-PCV2 antibodies. Piglets in the 3 vaccine groups (Groups 1 to 3) were injected intramuscularly with 1 ml of 3 different lots of inactivated PCV2 H strain vaccine, respectively. Two weeks after the primary immunization (p.i.), the piglets were boosted with the same dose of the vaccine. Piglets in Group 4 were unvaccinated and served as negative control. At 5 weeks after the primary immunization, all the piglets were challenged with PCV2 H strain (virulent strain) virus stock at a dose of $10^{6.0}$ 50% tissue culture infective doses per ml ($10^{6.0}$ $TCID_{50}$/ml). Each piglet was challenged intranasally with 1 ml of the virus stock and intramuscularly with 2 ml of the virus stock. Serum and nasal swab samples were collected at 7, 11, 19, and 25 days after challenge to detect PCV2 viremia by PCR.

2. Detection of PCV2 Viremia by PCR

Viral DNA levels in the pig serum samples collected after PCV2 challenge were determined using PCR. Viral DNA was extracted with DNAzol® reagent. First, 400 μl of DNAzol® reagent was added to 200 μl of serum, and the mixture was centrifuged at 12,000 rpm/min for 15 minutes. The supernatant was mixed with a double volume of absolute ethanol to precipitate DNA. After the mixture was centrifuged at 12,000 rpm/min for 15 minutes, the supernatant was discarded. The DNA pellet was washed with 75% ethanol, centrifuged at 12,000 rpm/min for 15 minutes to remove the ethanol, and finally dissolved in 8 mM NaOH.

PCR primers used to detect PCV2 viremia have the following sequences.

```
                                        (SEQ ID No. 8)
PCV2-F1:     5' GTGAAGTGGTATTTTGGTGCC 3'

                                        (SEQ ID No. 9)
PCV2-R1:     5' GTCTTCCAATCACGCTTCTGC 3'
```

PCV2-F1 (forward) and PCV2-R1 (reverse) primers were used to amplify a 284 bp fragment from the ORF1 of PCV2. The PCR mixture with a final volume of 25 μl contained 1 μl of forward primers, 1 μl of reverse primers, 1.5 μl of 25 mM $Mg^{2+}$, 2.0 μl of 2.5 mM dNTPs, 2.5 μl of 10×$Mg^{2+}$ free buffer, 0.2 μl of Taq DNA polymerase, 11.8 μl distilled water, and 5 μl template DNA. The PCR reaction started with an initial step of pre-heating the PCR mixture at 95° C. for 5 minutes, and amplification of DNA was carried out by 38 cycles with the following parameters; denaturing at 94° C. for 30 seconds, annealing at 55° C. for 30 seconds, and elongating at 72° C. for 30 seconds. The PCR reaction was completed with a final extension step of 5 minutes at 72° C. and then kept at 4° C. PCR products were next analyzed on a 1% agarose gel and visualized by ethidium bromide staining.

In addition, another pair of PCR primers used to detect PCV2 viremia has the following sequences.

```
PCV2-F2:  5' TGTTGGCGAGGAGGGTAATG '3 (SEQ ID No. 10)

PCV2-R2:  5' TGGGACAGCAGTTGAGGAGT '3 (SEQ ID No. 11)
```

PCV2-F2 (forward) and PCV2-R2 (reverse) primers were used to amplify a 676 bp fragment from PCV2.

3. Anatomy and Pathological Analysis

At 25 days after challenge, piglets were sacrificed and anatomized to observe pathological abnormalities in organs and collect lymph nodes and lungs. Tissue samples were fixed in 4% formaldehyde, embedded in paraffin, and then sectioned. Tissue sections were stained with hematoxylin and eosin (H&E) and viewed with a microscope.

4. Results 4.1 Evaluation of Viremia

PCR results showed that at 25 days after challenge, the occurrence of viremia in vaccinated piglets (Groups 1 to 3) was 40 to 60% lower than the occurrence in unvaccinated piglets (Group 4) (Table 6). The results indicated that the inactivated PCV2 H strain vaccine of the present invention were able to induce immunity in pigs, reduce the severity and duration of viremia in pigs, and protect pigs from PCV2 infection.

TABLE 6

Viremia in pig serum measured by PCR

| Group | Before challenge | days post challenge 7 | 11 | 19 | 25 |
|---|---|---|---|---|---|
| Group 1 | 0/5[a] | 2/5 | 2/5 | 1/5 | 1/5 |
| Group 2 | 0/5 | 2/5 | 1/5 | 0/5 | 0/5 |
| Group 3 | 0/5 | 3/5 | 2/5 | 1/5 | 1/5 |
| Group 4 (Control) | 0/5 | 4/5 | 3/5 | 4/5 | 3/5 |

[a]The denominators represent numbers of tested piglets, and the numerators represents numbers of piglets with viremia.

4.2 Histopathological Examination

Piglets were sacrificed and anatomized at 25 days after challenge. Enlargement of inguinal, mediastinal, and mesenteric lymph nodes were found in 2 unvaccinated piglets, and the sections of the lymph nodes were pale. Another unvaccinated piglet had non-collapsed, rubbery lungs, pulmonary edema, and white-spotted kidneys. All vaccinated piglets showed no gross pathological abnormality (Table 7).

TABLE 7

Pathological abnormalities in vaccinated and unvaccinated piglets

| Group | Pathological abnormality: Enlargement of lymph nodes | Pulmonary edema | White-spotted kidneys | Slight enlargement of spleen | Other abnormality[b] |
|---|---|---|---|---|---|
| Group 1 | 0/5[a] | 0/5 | 0/5 | 0/5 | 0/5 |
| Group 2 | 0/5 | 0/5 | 0/5 | 0/5 | 0/5 |
| Group 3 | 0/5 | 0/5 | 0/5 | 0/5 | 0/5 |
| Group 4 (Control) | 2/5 | 1/5 | 1/5 | 1/5 | 0/5 |

[a]The denominators represent numbers of anatomized piglets, and the numerators represents numbers of piglets with pathological abnormalities.

[b]Other abnormalities includes slight enlargement of liver or gallbladder, and intestinal tympanites.

Table 8 shows the results of microscopically histopathological examination of tissue sections and the results of evaluation of PCV2 viremia by PCR. Histopathological lesions in lymph nodes, such as lymphocyte depletion and macrophage infiltration were observed in almost all the unvaccinated piglets (Group 4), and all of the lymph nodes sampled from unvaccinated piglets were positive for PCV2 viremia. In addition, histopathological lesions in lungs, such as inflammatory cell infiltration, were observed in 3 unvaccinated piglets, and 2 of the lung tissues sampled from the unvaccinated piglets were positive for PCV2 viremia. Compared with the unvaccinated piglets, vaccinated piglets exhibited a significant reduction in histopathological lesions and PCV2 viremia. Histopathological lesions in lymph nodes were observed in only 1 vaccinated piglet (pig no. A4) out of 15 (Groups 1 to 3), and lymph nodes sampled from the vaccinated piglet (pig no. A4) were the only lymph nodes positive for PCV2 viremia. The results indicated that the inactivated PCV2 H strain vaccine of the present invention was able to protect pigs from PCV2 infection, and the protection rate was 80%~100%.

TABLE 8

Microscopically histopathological examination of tissue sections and evaluation of PCV2 viremia by PCR after PCV2 challenge

| Group | Pig No. | Lymph nodes: Gross pathological alterations | Lymphocyte depletion | Macrophage infiltration | PCR | Lungs: Gross pathological alterations | Inflammatory cell infiltration | PCR | Incidence of PWMS | Protection rate (%) |
|---|---|---|---|---|---|---|---|---|---|---|
| Group 1 | A1 | – | – | – | – | – | – | – | – | |
| | A2 | – | – | – | – | – | – | – | – | |
| | A3 | – | – | – | – | – | – | – | – | |
| | A4 | – | + | + | + | – | – | – | + | |
| | A5 | – | – | – | – | – | – | – | – | |
| | Subtotal | 1/5 | 1/5 | 0/5 | 1/5 | 0/5 | 0/5* | 0/5* | 1/5 | 80 |
| Group 2 | B1 | – | – | – | – | – | – | – | – | |
| | B2 | – | – | – | – | – | – | – | – | |
| | B3 | – | – | – | – | – | – | – | – | |
| | B4 | – | – | – | – | – | – | – | – | |
| | B5 | – | – | – | – | – | – | – | – | |
| | Subtotal | 0/5 | 0/5 | 0/5 | 0/5 | 0/5 | 0/5 | 0/5 | 0/5 | 100 |

TABLE 8-continued

Microscopically histopathological examination of tissue sections and evaluation of PCV2 viremia by PCR after PCV2 challenge

| | | Lymph nodes | | | | Lungs | | | | |
|---|---|---|---|---|---|---|---|---|---|---|
| Group | Pig No. | Gross pathological alterations | Lymphocyte depletion | Macrophage infiltration | PCR | Gross pathological alterations | Inflammatory cell infiltration | PCR | Incidence of PWMS | Protection rate (%) |
| Group 3 | C1 | − | − | − | − | − | − | − | − | |
| | C2 | − | − | − | − | − | − | − | − | |
| | C3 | − | − | − | − | − | − | − | − | |
| | C4 | − | − | − | − | − | − | − | − | |
| | C5 | − | − | − | − | − | − | − | − | |
| | Subtotal | 0/5 | 0/5 | 0/5 | 0/5 | 0/5 | 0/5 | 0/5 | 0/5 | 100 |
| Group 4 | D1 | + | + | + | + | − | + | − | + | |
| (Control) | D2 | + | + | + | + | + | + | + | + | |
| | D3 | − | + | + | + | − | + | + | + | |
| | D4 | − | + | + | + | − | − | − | + | |
| | D5 | − | + | − | + | − | − | − | + | |
| | Subtotal | 2/5 | 5/5 | 4/5 | 5/5 | 1/5 | 3/5 | 2/5 | 5/5 | |

*The denominators represent numbers of anatomized piglets, and the numerators represent numbers of piglets with pathological abnormalities.

Based on all of the results, the inactivated PCV2 H strain vaccine of the present invention effectively induced immunity in pigs, protected vaccinated pigs from PCV2 infection, reduced the severity and duration of viremia in pigs, minimized clinical symptoms, and increased body weight gain.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

What is claimed is:

1. An immunogenic composition, comprising an inactivated form of porcine circovirus type 2 (PCV2) virus, wherein the porcine circovirus type 2 (PCV2) virus comprises the genome sequence of SEQ ID NO: 1, and is inactivated by at least one of formaldehyde, paraformaldehyde, beta-propiolactone (BPL), and binary ethyleneimine (BEI).

2. The immunogenic composition of claim 1, further comprising a pharmaceutically acceptable vehicle.

3. The immunogenic composition of claim 2, wherein the pharmaceutically acceptable vehicle is an adjuvant.

4. The immunogenic composition of claim 1, further comprising at least one pathogen antigen selected from the group consisting of antigen of Swine influenza virus (SIV), antigen of porcine reproductive and respiratory syndrome virus (PRRSV), antigen of mycoplasma, antigen of porcine parvovirus (PPV), antigen of erysipelas, and antigen of pseudorabies virus.

5. A porcine circovirus type 2 (PCV2) test kit, comprising an inactivated form of porcine circovirus type 2 (PCV2) virus, wherein the PCV2 virus comprises the genome sequence of SEQ ID NO: 1, and is inactivated by at least one of formaldehyde, paraformaldehyde, beta-propiolactone (BPL), and binary ethyleneimine (BEI).

6. The porcine circovirus type 2 (PCV2) test kit of claim 5, wherein the inactivated form of PCV2 virus is deposited on a plate.

* * * * *

```
                          SEQUENCE LISTING

<160> NUMBER OF SEQ ID NOS: 14

<210> SEQ ID NO 1
<211> LENGTH: 1767
<212> TYPE: DNA
<213> ORGANISM: Porcine circovirus

<400> SEQUENCE: 1

accagcgcac ttcggcagcg gcagcacctc ggcagcacct cagcagcaac atgcccagca      60

agaagagtgg aagaagcgga ccccaaccac ataaaaggtg ggtgttcacg ctgaataatc     120

cttccgaaga cgagcgcaag aaaatacggg agctcccaat ctccctattt gattatttta     180

ttgttggcga ggaaggtaat gaggagggcc gaacacccca cctacagggg ttcgctaatt     240

ttgtgaagaa gcaaactttt aataaagtga agtggtattt tggtgcccgc tgccacatcg     300

agaaagcgaa aggaacagat cagcagaata aagaatattg cagtaaagaa ggcaacttac     360

tgatagaatg tggagctcct agatctcaag gacaacggag tgacctctct actgctgtga     420

gtaccttgtt ggagagcggg agtctggtga ccgttgcaga gcagcaccct gtaacgtttg     480

tcagaaattt ccgcgggctg gctgaacttt tgaaagtgag cgggaaaatg cagaagcgtg     540

attggaagac gaatgtacac gtcattgtgg ggccacctgg gtgtggcaaa agcaaatggg     600

ctgctaattt tgcagacccg gaaaccacat actggaaacc acctagaaac aagtggtggg     660

atggttacca tggtgaagaa gtggttgtta ttgatgactt ttatggctgg ctgccgtggg     720

atgatctact gagactctgt gatcgatatc ctttgactgt tgagactaaa ggtggaactg     780

tacctttttt ggcccgcagt attctgatta ccagcaatca gaccccgttg gaatggtact     840

cctcaactgc tgtcccagct gtagaagctc tctatcggag gattacttcc ttggtatttt     900

ggaagaatgc tacagaacaa tccacggagg aagggggcca gttcgtcacc ctttcccccc     960

catgccctga atttccatat gaaataaatt actgagtctt ttttatcact tcgtaatggt    1020
```

-continued

```
ttttattatt cacttagggt taagtggggg gtctttaaga ttaaattctc tgaattgtac   1080

atacatggtt atacggatat tgtagtcctg gtcgtatata ctgttttcga acgcagtgcc   1140

gaggcctaca tggtctacat ttccagtagt ttgtagtctc agccagagtt gatttctttt   1200

gttattgggt tggaagtaat cgattgtcct atcaaggaca ggtttcgggg taaagtaccg   1260

ggagtggtag gagaagggct gggttatggt atggcgggag gagtagttta cataggggtc   1320

ataggttagg gcattggcct ttgttacaaa gttatcatct agaataacag cagtggagct   1380

cactcccctg tcaccctggg tgattgggga gcagggccag aattcaacct taaccttcct   1440

tattctgtag tattcaaagg gcacagtgag gggcttgag cccctcctg ggggaagaaa   1500

atcattaata ttaaatctca tcatgtccac attccaggag ggcgttctga ctgtggtttt   1560

cttgacagta taaccgatgg tgcgggagag gcgggtgttg aagatgccat tttccttct   1620

ccagcggtaa cggtggcggg ggtggactag ccaggggcgg cggcggagga tctggccaag   1680

atggctgcgg gggcggtgtc ttcgtctgcg gtaacgcctc cttggatacg tcatcgctga   1740

aaacgaaaga agtgcgctgt aagtatt                                        1767


<210> SEQ ID NO 2
<211> LENGTH: 945
<212> TYPE: DNA
<213> ORGANISM: Porcine circovirus

<400> SEQUENCE: 2

atgcccagca agaagagtgg aagaagcgga ccccaaccac ataaaaggtg ggtgttcacg     60

ctgaataatc cttccgaaga cgagcgcaag aaaatacggg agctcccaat ctccctattt    120

gattatttta ttgttggcga ggaaggtaat gaggagggcc gaacacccca cctacagggg    180

ttcgctaatt ttgtgaagaa gcaaactttt aataaagtga agtggtattt tggtgcccgc    240

tgccacatcg agaaagcgaa aggaacagat cagcagaata aagaatattg cagtaaagaa    300

ggcaacttac tgatagaatg tggagctcct agatctcaag gacaacggag tgacctctct    360

actgctgtga gtaccttgtt ggagagcggg agtctggtga ccgttgcaga gcagcaccct    420

gtaacgtttg tcagaaattt ccgcgggctg gctgaacttt tgaaagtgag cgggaaaatg    480

cagaagcgtg attggaagac gaatgtacac gtcattgtgg ggccacctgg gtgtggcaaa    540

agcaaatggg ctgctaattt tgcagacccg gaaaccacat actggaaacc acctagaaac    600

aagtggtggg atggttacca tggtgaagaa gtggttgtta ttgatgactt ttatggctgg    660

ctgccgtggg atgatctact gagactctgt gatcgatatc ctttgactgt tgagactaaa    720

ggtggaactg taccttttt ggcccgcagt attctgatta ccagcaatca gaccccgttg    780

gaatggtact cctcaactgc tgtcccagct gtagaagctc tctatcggag gattacttcc    840

ttggtatttt ggaagaatgc tacagaacaa tccacggagg aagggggcca gttcgtcacc    900

ctttcccccc catgccctga atttccatat gaaataaatt actga                    945


<210> SEQ ID NO 3
<211> LENGTH: 314
<212> TYPE: PRT
<213> ORGANISM: Porcine circovirus

<400> SEQUENCE: 3

Met Pro Ser Lys Lys Ser Gly Arg Ser Gly Pro Gln Pro His Lys Arg
1               5                   10                  15

Trp Val Phe Thr Leu Asn Asn Pro Ser Glu Asp Glu Arg Lys Lys Ile
            20                  25                  30
```

```
Arg Glu Leu Pro Ile Ser Leu Phe Asp Tyr Phe Ile Val Gly Glu Glu
        35                  40                  45

Gly Asn Glu Glu Gly Arg Thr Pro His Leu Gln Gly Phe Ala Asn Phe
    50                  55                  60

Val Lys Lys Gln Thr Phe Asn Lys Val Lys Trp Tyr Phe Gly Ala Arg
65                  70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Ile Glu Cys Gly Ala Pro Arg Ser
            100                 105                 110

Gln Gly Gln Arg Ser Asp Leu Ser Thr Ala Val Ser Thr Leu Leu Glu
        115                 120                 125

Ser Gly Ser Leu Val Thr Val Ala Glu Gln His Pro Val Thr Phe Val
    130                 135                 140

Arg Asn Phe Arg Gly Leu Ala Glu Leu Leu Lys Val Ser Gly Lys Met
145                 150                 155                 160

Gln Lys Arg Asp Trp Lys Thr Asn Val His Val Ile Val Gly Pro Pro
                165                 170                 175

Gly Cys Gly Lys Ser Lys Trp Ala Ala Asn Phe Ala Asp Pro Glu Thr
            180                 185                 190

Thr Tyr Trp Lys Pro Pro Arg Asn Lys Trp Trp Asp Gly Tyr His Gly
        195                 200                 205

Glu Glu Val Val Val Ile Asp Asp Phe Tyr Gly Trp Leu Pro Trp Asp
    210                 215                 220

Asp Leu Leu Arg Leu Cys Asp Arg Tyr Pro Leu Thr Val Glu Thr Lys
225                 230                 235                 240

Gly Gly Thr Val Pro Phe Leu Ala Arg Ser Ile Leu Ile Thr Ser Asn
                245                 250                 255

Gln Thr Pro Leu Glu Trp Tyr Ser Ser Thr Ala Val Pro Ala Val Glu
            260                 265                 270

Ala Leu Tyr Arg Arg Ile Thr Ser Leu Val Phe Trp Lys Asn Ala Thr
        275                 280                 285

Glu Gln Ser Thr Glu Glu Gly Gly Gln Phe Val Thr Leu Ser Pro Pro
    290                 295                 300

Cys Pro Glu Phe Pro Tyr Glu Ile Asn Tyr
305                 310
```

```
<210> SEQ ID NO 4
<211> LENGTH: 705
<212> TYPE: DNA
<213> ORGANISM: Porcine circovirus

<400> SEQUENCE: 4

atgacgtatc caaggaggcg ttaccgcaga cgaagacacc gcccccgcag ccatcttggc      60

cagatcctcc gccgccgccc ctggctagtc cacccccgcc accgttaccg ctggagaagg     120

aaaaatggca tcttcaacac ccgcctctcc cgcaccatcg gttatactgt caagaaaacc     180

acagtcagaa cgccctcctg gaatgtggac atgatgagat ttaatattaa tgattttctt     240

cccccaggag ggggctcaag cccccctcact gtgccctttg aatactacag aataaggaag     300

gttaaggttg aattctggcc ctgctcccca atcacccagg gtgacagggg agtgagctcc     360

actgctgtta ttctagatga taactttgta acaaaggcca atgccctaac ctatgacccc     420

tatgtaaact actcctcccg ccataccata acccagccct tctcctacca ctcccggtac     480
```

-continued

```
tttaccccga aacctgtcct tgataggaca atcgattact tccaacccaa taacaaaaga    540

aatcaactct ggctgagact acaaactact ggaaatgtag accatgtagg cctcggcact    600

gcgttcgaaa acagtatata cgaccaggac tacaatatcc gtataaccat gtatgtacaa    660

ttcagagaat ttaatcttaa agaccccccca cttaacccta agtga                     705


<210> SEQ ID NO 5
<211> LENGTH: 234
<212> TYPE: PRT
<213> ORGANISM: Porcine circovirus

<400> SEQUENCE: 5

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Ser Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Ser Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230


<210> SEQ ID NO 6
<211> LENGTH: 315
<212> TYPE: DNA
<213> ORGANISM: Porcine circovirus

<400> SEQUENCE: 6

atggtaacca tcccaccact tgtttctagg tggtttccag tatgtggttt ccgggtctgc     60

aaaattagca gcccatttgc ttttgccaca cccaggtggc cccacaatga cgtgtacatt    120

cgtcttccaa tcacgcttct gcattttccc gctcactttc aaaagttcag ccagcccgcg    180

gaaatttctg acaaacgtta cagggtgctg ctctgcaacg gtcaccagac tcccgctctc    240

caacaaggta ctcacagcag tagagaggtc actccgttgt ccttgagatc taggagctcc    300
```

acattctatc agtaa 315

<210> SEQ ID NO 7
<211> LENGTH: 104
<212> TYPE: PRT
<213> ORGANISM: Porcine circovirus

<400> SEQUENCE: 7

```
Met Val Thr Ile Pro Pro Leu Val Ser Arg Trp Phe Pro Val Cys Gly
1               5                   10                  15

Phe Arg Val Cys Lys Ile Ser Ser Pro Phe Ala Phe Ala Thr Pro Arg
            20                  25                  30

Trp Pro His Asn Asp Val Tyr Ile Arg Leu Pro Ile Thr Leu Leu His
        35                  40                  45

Phe Pro Ala His Phe Gln Lys Phe Ser Gln Pro Ala Glu Ile Ser Asp
    50                  55                  60

Lys Arg Tyr Arg Val Leu Leu Cys Asn Gly His Gln Thr Pro Ala Leu
65                  70                  75                  80

Gln Gln Gly Thr His Ser Ser Arg Glu Val Thr Pro Leu Ser Leu Arg
                85                  90                  95

Ser Arg Ser Ser Thr Phe Tyr Gln
            100
```

<210> SEQ ID NO 8
<211> LENGTH: 21
<212> TYPE: DNA
<213> ORGANISM: Artificial Sequence
<220> FEATURE:
<223> OTHER INFORMATION: Primer/ probe for detecting Porcine Circovirus Type 2

<400> SEQUENCE: 8
gtgaagtggt attttggtgc c 21

<210> SEQ ID NO 9
<211> LENGTH: 21
<212> TYPE: DNA
<213> ORGANISM: Artificial Sequence
<220> FEATURE:
<223> OTHER INFORMATION: Primer/ probe for detecting Porcine Circovirus Type 2

<400> SEQUENCE: 9
gtcttccaat cacgcttctg c 21

<210> SEQ ID NO 10
<211> LENGTH: 20
<212> TYPE: DNA
<213> ORGANISM: Artificial Sequence
<220> FEATURE:
<223> OTHER INFORMATION: Primer/ probe for detecting Porcine Circovirus Type 2

<400> SEQUENCE: 10
tgttggcgag gagggtaatg 20

<210> SEQ ID NO 11
<211> LENGTH: 20
<212> TYPE: DNA
<213> ORGANISM: Artificial Sequence
<220> FEATURE:
<223> OTHER INFORMATION: Primer/ probe for detecting Porcine Circovirus Type 2

<400> SEQUENCE: 11
tgggacagca gttgaggagt 20

<210> SEQ ID NO 12
<211> LENGTH: 234
<212> TYPE: PRT
<213> ORGANISM: Porcine circovirus
<300> PUBLICATION INFORMATION:
<308> DATABASE ACCESSION NUMBER: GenBank: ABV21950.1
<309> DATABASE ENTRY DATE: 2007-09-16
<313> RELEVANT RESIDUES IN SEQ ID NO: (1)..(234)

<400> SEQUENCE: 12

```
Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 13
<211> LENGTH: 234
<212> TYPE: PRT
<213> ORGANISM: Porcine circovirus
<300> PUBLICATION INFORMATION:
<308> DATABASE ACCESSION NUMBER: GenBank: ADK34046.1
<309> DATABASE ENTRY DATE: 2010-07-21
<313> RELEVANT RESIDUES IN SEQ ID NO: (1)..(234)

<400> SEQUENCE: 13

```
Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30
```

```
Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Ile Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230


<210> SEQ ID NO 14
<211> LENGTH: 234
<212> TYPE: PRT
<213> ORGANISM: Porcine circovirus
<300> PUBLICATION INFORMATION:
<308> DATABASE ACCESSION NUMBER: GenBank: ADD25772.1
<309> DATABASE ENTRY DATE: 2012-08-31
<313> RELEVANT RESIDUES IN SEQ ID NO: (1)..(234)

<400> SEQUENCE: 14

Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Met Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
```

-continued

```
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```